United States Patent
Amanatullah (10) Patent No.: US 11,857,423 B2
(45) Date of Patent: Jan. 2, 2024

(54) OFF-CENTER LINER FOR ACETABULAR CUP

(71) Applicant: Arthrology Consulting, LLC, Menlo Park, CA (US)

(72) Inventor: Derek Amanatullah, Menlo Park, CA (US)

(73) Assignee: ARTHROLOGY CONSULTING, LLC, Menlo Park, CA (US)

( * ) Notice: Subject to any disclaimer, the term of this patent is extended or adjusted under 35 U.S.C. 154(b) by 115 days.

(21) Appl. No.: 17/455,130

(22) Filed: Nov. 16, 2021

(65) Prior Publication Data
US 2023/0149174 A1    May 18, 2023

(51) Int. Cl.
*A61F 2/34* (2006.01)
*A61F 2/46* (2006.01)
*A61F 2/30* (2006.01)

(52) U.S. Cl.
CPC .............. *A61F 2/34* (2013.01); *A61F 2/4609* (2013.01); *A61F 2002/30617* (2013.01); *A61F 2002/3453* (2013.01); *A61F 2002/4681* (2013.01)

(58) Field of Classification Search
CPC ...................... A61F 2/34; A61F 2/4609; A61F 2002/30617; A61F 2002/4681
See application file for complete search history.

(56) References Cited

U.S. PATENT DOCUMENTS

| | | |
|---|---|---|
| 4,123,806 A | 11/1978 | Amstutz et al. |
| 4,327,449 A | 5/1982 | Charnley |
| 4,437,193 A | 3/1984 | Oh |
| 4,623,352 A | 11/1986 | Oh |
| 4,795,469 A | 1/1989 | Oh |
| 4,883,490 A | 11/1989 | Oh |
| 4,955,919 A | 9/1990 | Pappas et al. |
| 5,133,764 A | 7/1992 | Pappas et al. |
| 5,376,122 A | 12/1994 | Pappas et al. |
| 5,507,824 A * | 4/1996 | Lennox ............... A61F 2/4684 623/22.25 |
| 5,527,317 A | 6/1996 | Ashby et al. |
| 5,571,200 A | 11/1996 | Cohen et al. |
| 5,879,399 A | 3/1999 | Church |
| 6,352,559 B1 | 3/2002 | Church |
| 6,520,995 B2 | 2/2003 | Church |
| 6,537,321 B1 | 3/2003 | Horber |
| 6,926,740 B2 | 8/2005 | Lewis et al. |
| 7,022,142 B2 | 4/2006 | Johnson |
| 7,074,241 B2 | 7/2006 | McKinnon |
| 7,264,636 B2 | 9/2007 | Lewis |
| 7,291,177 B2 | 11/2007 | Gibbs |
| 7,402,177 B2 | 7/2008 | Jones et al. |
| 7,572,296 B2 | 8/2009 | Scott et al. |

(Continued)

*Primary Examiner* — Brian A Dukert
(74) *Attorney, Agent, or Firm* — Knobbe, Martens, Olson & Bear, LLP (57) ABSTRACT

Off-center liners can be used with an acetabular cup in hip replacement or revision surgical procedures. The liners (of metal or plastic) can be laterally spaced from the acetabular cup, angled relative to the acetabular cup and/or have an opening that is offset relative to the axis of the acetabular cup. The liners have an orientation indicator that identifies where the liner should be impacted (e.g., impaction location or point) by the impactor to ensure the liner is impacted in a square manner relative to the acetabular cup.

20 Claims, 7 Drawing Sheets

(56) References Cited

U.S. PATENT DOCUMENTS

| | | |
|---|---|---|
| 7,682,398 B2 | 3/2010 | Croxton et al. |
| 7,713,306 B2 | 5/2010 | Gibbs |
| 7,846,212 B2 | 12/2010 | Lewis et al. |
| 7,955,395 B2 | 6/2011 | Shea et al. |
| 8,123,814 B2 | 2/2012 | Meridew et al. |
| 8,211,184 B2 | 7/2012 | Ries et al. |
| 8,529,633 B2 | 9/2013 | Lazennec et al. |
| 8,551,181 B2 | 10/2013 | Meridew et al. |
| 8,574,306 B2 | 11/2013 | Ries |
| 8,597,364 B2 | 12/2013 | Lewis et al. |
| 8,679,188 B2 | 3/2014 | Shea et al. |
| 9,017,415 B2 | 4/2015 | Coustance et al. |
| 9,017,416 B2 | 4/2015 | McMinn |
| 9,283,079 B2 | 3/2016 | McMinn |
| 9,289,313 B2 * | 3/2016 | Preuss ................ A61B 17/8872 |
| 9,375,316 B2 | 6/2016 | Meridew et al. |
| 9,649,193 B2 | 5/2017 | McMinn |
| 9,956,081 B2 | 5/2018 | McMinn |
| 9,980,829 B2 | 5/2018 | Miles et al. |
| 10,463,506 B2 | 11/2019 | Kelman et al. |
| 10,966,837 B2 | 4/2021 | McMinn |
| 11,013,604 B2 | 5/2021 | Rister et al. |
| 2006/0241780 A1 | 10/2006 | McKinnon |
| 2007/0179629 A1 | 8/2007 | Murphy |
| 2012/0319332 A1 | 12/2012 | McMinn |
| 2016/0287395 A1 | 10/2016 | Khalili et al. |
| 2020/0008957 A1 | 1/2020 | Kelman et al. |
| 2020/0289292 A1 | 1/2020 | Kelman et al. |
| 2021/0137687 A1 | 5/2021 | Rister et al. |
| 2021/0177606 A1 | 6/2021 | Butler et al. |
| 2021/0177607 A1 | 6/2021 | Butler et al. |

* cited by examiner

OFF-CENTER LINER FOR ACETABULAR CUP

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Field

The present disclosure is directed to liners for an acetabular cup for use in hip joint replacement surgical procedures, and more particularly to off-center liners for an acetabular cup.

Description of the Related Art

Hip joint replacement surgical procedures involve the implantation of an acetabular cup in the pelvis bone that receives a liner and a head of a femoral stem implant that is inserted into the femur bone. Dual mobility liners made of plastic (e.g., of Polyethylene) are used with acetabular cups. However, existing liners made of plastic can lose material during use following implantation).

SUMMARY

In accordance with one aspect of the disclosure, off-center liners are provided for use with an acetabular cup in hip replacement or revision surgical procedures. The liners can in one implementation be made of metal. In another implementation, the liners can be made of a plastic material (e.g., Polyethylene). In still another implementation, the liners can be made of a ceramic material. The liners can be laterally spaced from the acetabular cup, angled relative to the acetabular cup and/or have an opening that is offset relative to the axis of the acetabular cup. The liners have an orientation indicator that identifies where the liner should be impacted (e.g., impaction location or point) by the impactor to ensure the liner is impacted in a square manner relative to the acetabular cup.

In accordance with one aspect of the disclosure, a liner for an acetabular cup is provided. The liner comprises a proximal surface, an outer convex surface configured to at least partially extend into an acetabular cup when the liner is seated in the acetabular cup, and a concave bearing surface recessed relative to the proximal surface and configured to receive a head of a femoral stem. One or more visual indicators on the liner are configured to identify a location for applying an impaction force on the liner so that the liner is impacted square relative to the acetabular cup.

In accordance with another aspect of the disclosure, a liner and impactor system for an acetabular cup is provided. The system comprises a liner comprising a proximal surface, an outer convex surface configured to at least partially extend into an acetabular cup when the liner is seated in the acetabular cup, and a concave bearing surface recessed relative to the proximal surface and configured to receive a head of a femoral stem. One or more visual indicators on the liner are configured to identify a location for applying an impaction force on the liner. The system also comprises an impactor having an impaction surface corresponding to one or both of the proximal surface and the concave bearing surface of the liner, the impactor configured to apply an impaction force on the liner so that the liner is impacted square relative to the acetabular cup.

In accordance with another aspect of the disclosure, a method for implanting a liner in an acetabular cup is provided. The method comprises evaluating a size of an acetabular hole, identifying a size of an acetabular cup for the acetabular hole, and preparing the acetabular hole to receive the acetabular cup. The method also comprises identifying a liner for use with the acetabular cup, inserting the acetabular cup in the acetabular hole, and inserting the liner in the acetabular cup. The method also comprises impacting the liner into place in the acetabular cup with an impactor square with the acetabular cup to seat the liner in the acetabular cup.

DETAILED DESCRIPTION

Disclosed herein are liners (e.g., metal liners, such as made of titanium, plastic liners, such as made of Polyethylene, ceramic liners) for use in a hip joint surgical procedure, such as hip joint revision surgery, where an acetabular cup is implanted in the acetabulum of the pelvis bone. The acetabular cup can at least partially receive the liner, which can at least partially receive a ball of a femoral stem implant, or can receive a second liner (e.g., made of plastic, such as Polyethylene) that can then receive the ball of the femoral stem implant. The liners disclosed below advantageously provide structural support to the ball of the femoral stem while inhibiting (e.g., preventing) loss of material as occurs with plastic liners. Additionally, the liners disclosed herein allow a smaller femoral stem head to be used with a same sized acetabular cup, with the head laterally displaced farther away from the bottom of the acetabular cup, which advantageously provides improved stability of the hip joint.

Figure 1:
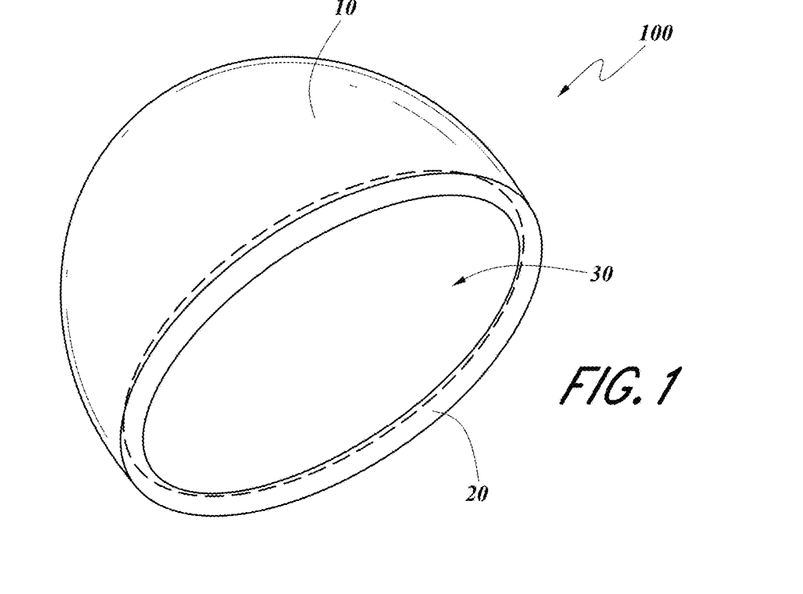
FIG. 1 is a schematic perspective view of an acetabular cup.

FIG. 1 shows a perspective view of an acetabular cup 100 having an outer convex surface 10, an outer rim 20 and an inner convex surface or bearing surface 30 that defines a cavity that receives a liner, such as the liners disclosed herein.

Figure 2A:
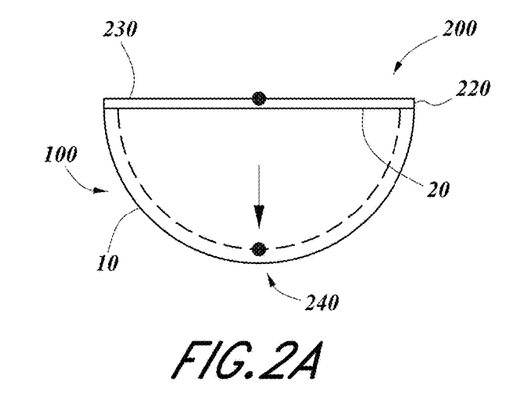
FIG. 2A is a schematic side view of the acetabular cup in FIG. 1 with a liner inserted in the acetabular cup flush with the acetabular cup.
Figure 2B:
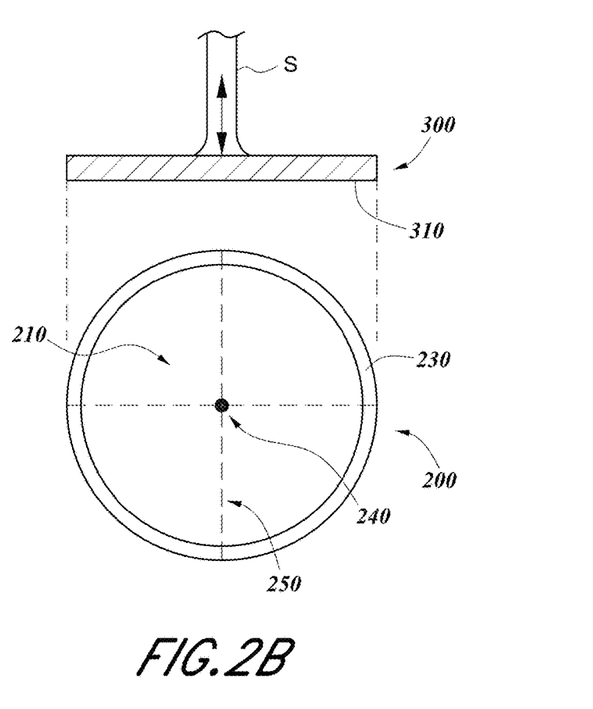
FIG. 2B is a schematic top view of the liner in FIG. 2A and a partial schematic side view of an impactor head surface to impact the liner.

FIG. 2A shows a liner 200 coupled to the acetabular cup 100 and FIG. 2B shows a top view of the liner 200 and an impactor 300 that can be used to impact the liner 200 into place in the acetabular cup 100. The liner 200 can sit flush with the acetabular cup 100 and have a proximal portion 220 that protrudes relative to the outer rim 20 of the acetabular cup 100. The liner 200 can also have a bearing surface 210 and an outer rim 230 that circumscribes the bearing surface 210. The outer rim 230 can extend a long a plane (e.g., be planar). The liner 200 can have one or more visual indications 240, 250 identifying the location of the impaction force for the liner 200 to be impacted square relative to the acetabular cup 100. The visual indicators can include an indicator 240 (e.g., cross-hairs, dot, sticker or removable layer) on the bearing surface 210. The visual indicators can also include one or more indicators 250 (e.g., etched lines, markings) on the outer rim 230 or bearing surface 210 that align with the indicator 240. The visual indicators can be in separate components (e.g., stickers), which can be removed after the impaction force is applied. In another implementation, the visual indicators can be made (e.g., etchings, grooves) in the material of the liner 200. In still another implementation, the visual indicators can be virtual (e.g., applied to or projected onto the liner 200 by a robotic system, such as by an imaging system of a robotic surgical system).

The impactor 300 has a shaft S and an impaction surface 310 corresponding to the liner 200. In the illustrated implementation, the impaction surface 310 is planar and corresponds to the planar outer rim 230 of the liner 200, so that the impactor 300 can apply a force square relative to the liner 200 to seat the liner 200 in the acetabular cup 100 (e.g., so the center of the impaction force that is applied is located at the location of the visual indicator 240). In one implementation, an outer diameter or dimension of the impaction surface 310 corresponds with an outer diameter of the outer rim 230 of the liner 200.

Figure 3A:
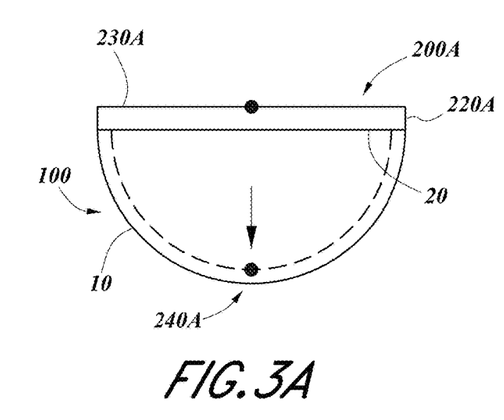
FIG. 3A is a schematic side view of the acetabular cup in FIG. 1 with a liner inserted in the acetabular cup laterally spaced relative to the acetabular cup.
Figure 3B:
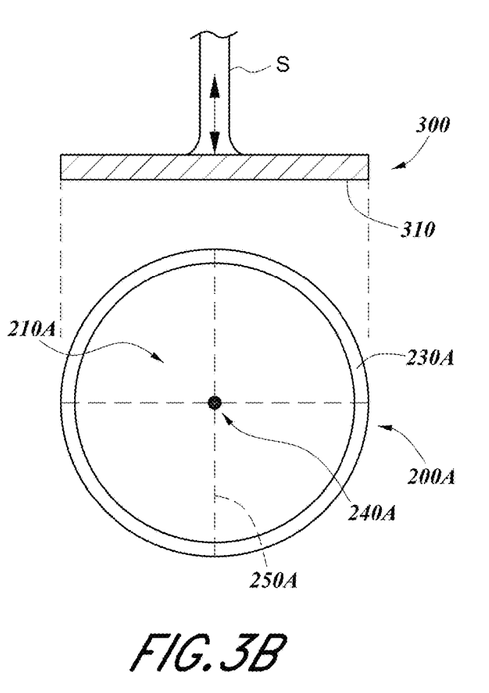
FIG. 3B is a schematic top view of the liner in FIG. 3A and a partial schematic side view of an impactor head surface to impact the liner.

FIG. 3A shows a liner 200A coupled to the acetabular cup 100 and FIG. 3B shows a top view of the liner 200A and the impactor 300, which can be used to impact the liner 200A into place in the acetabular cup 100. Some of the features of the liner 200A are similar to features of the liner 200 in FIGS. 2A-2B. Thus, reference numerals used to designate the various components of the liner 200A are identical to those used for identifying the corresponding components of the liner 200 in FIGS. 2A-2B, except that an "A" has been added to the numerical identifier. Therefore, the structure and description for the various features of the liner 200 in FIGS. 2A-2B are understood to also apply to the corresponding features of the liner 200A in FIGS. 3A-3B, except as described below.

The liner 200A differs from the liner 200 in that it's outer rim 230A is laterally spaced from the outer rim 20 by a larger amount than the liner 200. Similarly, the bearing surface 210A can be laterally spaced from a distal end of the acetabular cup 100 by a larger amount than the bearing surface 210 of the liner 200, allowing the head of the femoral stem implant to be further laterally spaced apart (as compared with the liner 200 and acetabular cup 100). The outer rim 230A of the liner 200A can be planar (e.g., extend along or be defined by a plane) so the same impactor 300 used for the liner 200 can be used for the liner 200A to apply an impaction force on the liner 200A square with the acetabular cup 100 (e.g., so the center of the impaction force that is applied is located at the location of the visual indicator 240).

Figure 4A:
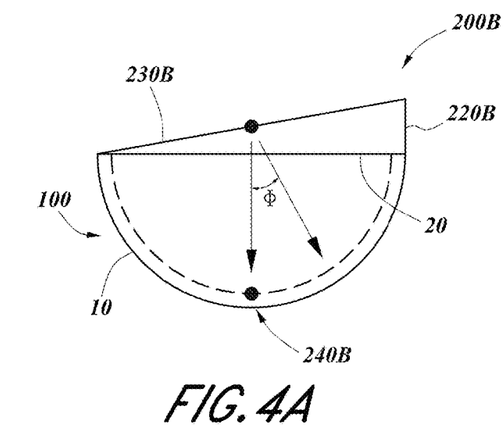
FIG. 4A is a schematic side view of the acetabular cup in FIG. 1 with a liner inserted in the acetabular cup, the liner having an angled face relative to the acetabular cup.
Figure 4B:
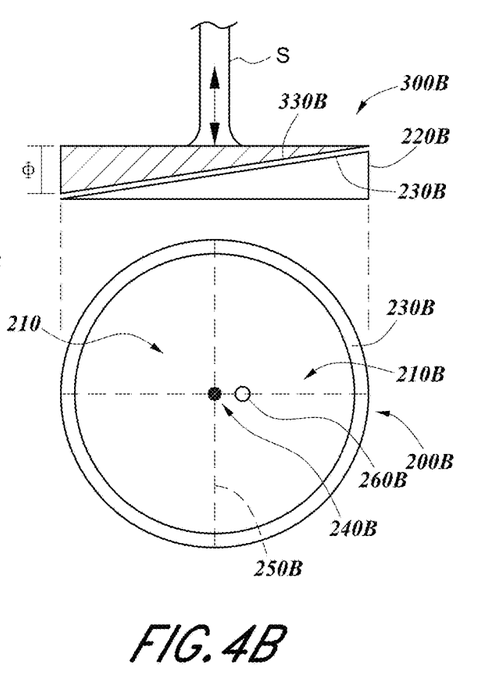
FIG. 4B is a schematic top view of the liner in FIG. 4A and a partial schematic side view of an impactor head surface to impact the liner.

FIG. 4A shows a liner 200B coupled to the acetabular cup 100 and FIG. 4B shows a top view of the liner 200B and an impactor 300B, which can be used to impact the liner 200B into place in the acetabular cup 100. Some of the features of the liner 200B and impactor 300B are similar to features of the liner 200 and impactor 300 in FIGS. 2A-2B. Thus, reference numerals used to designate the various components of the liner 200B and impactor 300B are identical to those used for identifying the corresponding components of the liner 200 and impactor 300 in FIGS. 2A-2B, except that a "B" has been added to the numerical identifier. Therefore, the structure and description for the various features of the liner 200 and impactor 300 in FIGS. 2A-2B are understood to also apply to the corresponding features of the liner 200B and impactor 300B in FIGS. 4A-4B, except as described below.

The liner 200B differs from the liner 200 in that the outer rim 230B (and therefore the face) of the liner 200B extends at an angle f relative to the outer rim 20 of the acetabular cup 100. The bearing surface 210B has visual indicators 240B, 250B for applying an impaction force on the liner 200B square with the acetabular cup 100 using an impactor 300B. The bearing surface 210B of the liner 200B can also have a visual indicator 260B indicating the offset location of the center of the bearing surface resulting from the angled outer rim 230B.

The impactor 300B has an impactor surface 310B corresponding to the outer rim 230B of the liner 200B. The impactor surface 310B can be angled at the same angle $\phi$ relative to the shaft S as the outer rim 230B is to the outer rim 20 of the acetabular cup 100. This advantageously allows the impactor 300B to apply an impaction force square on the outer rim 230B of the liner 200 relative to the acetabular cup 100 (e.g., so the center of the impaction force that is applied is located substantially at the location of the visual indicator 240B).

Figure 5A:
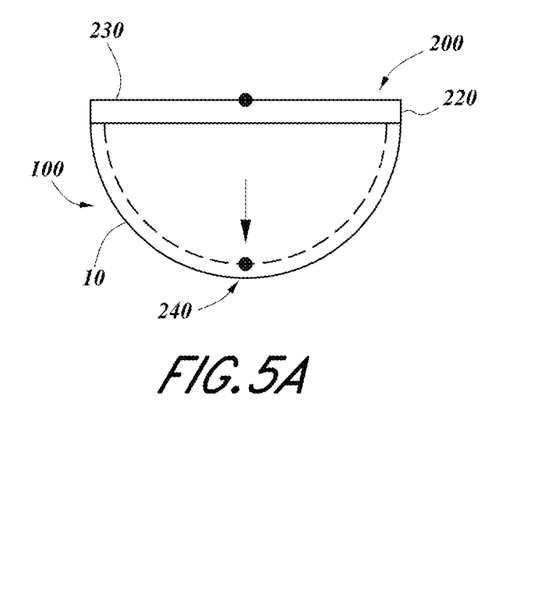
FIG. 5A is a schematic side view of the acetabular cup in FIG. 1 with a liner inserted in the acetabular cup, the liner being flush with the acetabular cup.
Figure 5B:
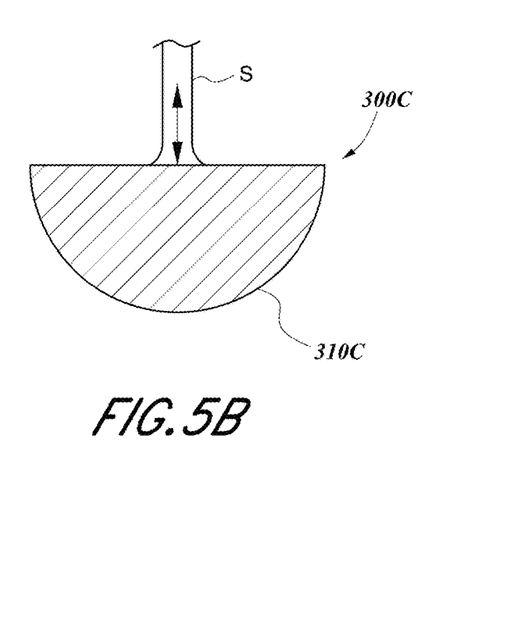
FIG. 5B is a schematic top view of the liner in FIG. 5A and a partial schematic side view of an impactor head surface to impact the liner.

FIG. 5A shows the liner 200 attached to the acetabular cup 100 and FIG. 5B shows an impactor 300C that can be used to impact the liner 200 into place in the acetabular cup 100. The impactor 300C can have a curved (e.g., convex, spherical) impactor surface 310C. The impactor 300C can be used instead of the impactor 300 to apply an impaction force on the liner 200 to seat the liner 200 in the acetabular cup. Unlike the impactor 300, which applies the impaction force on the outer rim 230 of the liner 200, the impactor 300C can be used to apply the impaction force on or proximate the visual indicator 240 so that the impactor 300C impacts the liner 200 square relative to the acetabular cup 100.

Figure 6:
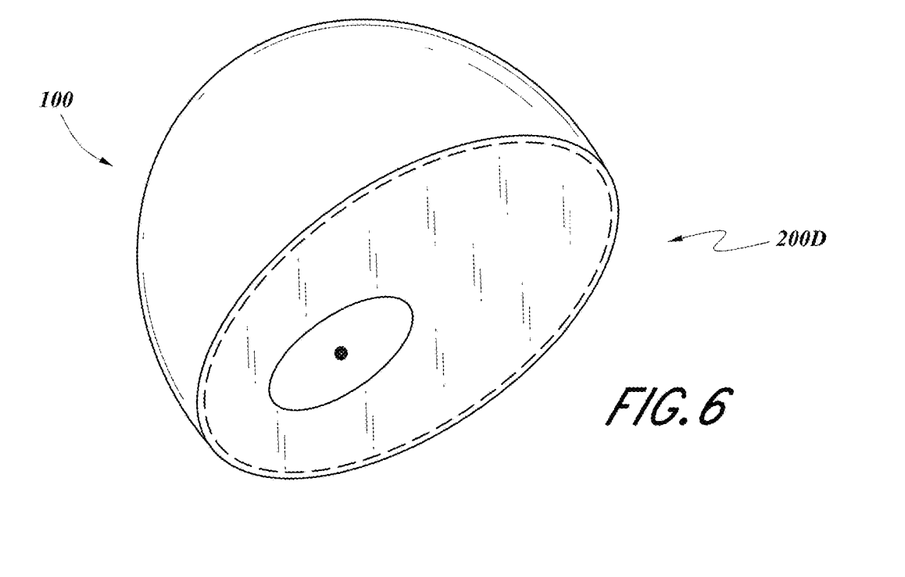
FIG. 6 is a perspective view of an acetabular cup with a liner having an offset opening for the femoral head of an implant.
Figure 7A:
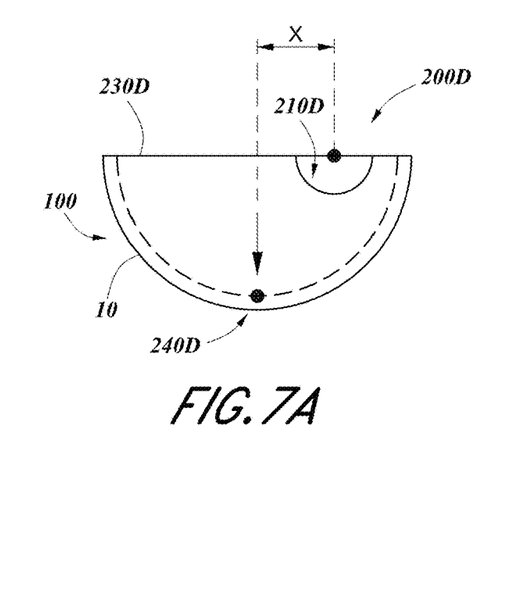
FIG. 7A is a schematic cross-sectional side view of the acetabular cup and liner in FIG. 6.
Figure 7B:
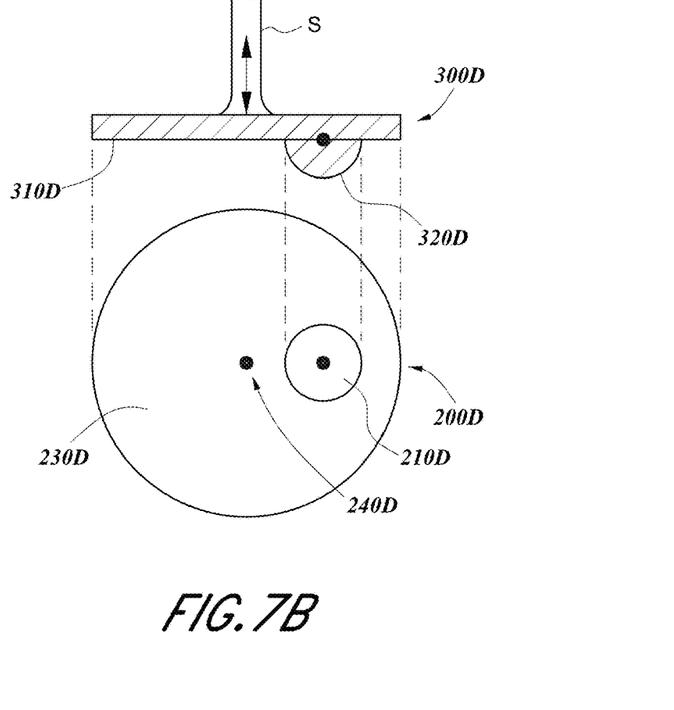
FIG. 7B is a schematic top view of the liner in FIG. 7A and a partial schematic side view of an impactor head surface to impact the liner.

FIG. 6 shows a perspective view of a liner 200D attached to the acetabular cup 100. FIG. 7A shows a cross-sectional side view of the liner 200D coupled to the acetabular cup 100 and FIG. 7B shows a top view of the liner 200D and an impactor 300D, which can be used to impact the liner 200D into place in the acetabular cup 100. Some of the features of the liner 200D are similar to features of the liner 200 in FIGS. 2A-2B. Thus, reference numerals used to designate the various components of the liner 200D are identical to those used for identifying the corresponding components of the liner 200 in FIGS. 2A-2B, except that a "D" has been added to the numerical identifier. Therefore, the structure and description for the various features of the liner 200 in FIGS. 2A-2B are understood to also apply to the corresponding features of the liner 200D in FIGS. 6-7B, except as described below. FIGS. 6-7B are not to scale and are exaggerated to show that the center of the bearing surface of the liner 200D, and therefore the head of the femoral stem implant received therein, would be offset or off-center relative to the center of the acetabular cup 100.

The liner 200D differs from the liner 200 in that bearing surface 210D (e.g., concave) of the liner 200D is offset from a centerline of the acetabular cup 100 so that the bearing surface 210D is not coaxial with the bearing surface 30 of the acetabular cup 100, and so that a center of the head of the femoral stem implant that is received by the bearing surface 210D would be offset or off-center relative to the axis or center of the acetabular cup 100. As shown in FIG. 7A, the axis of the bearing surface 210D can be offset by a distance X from a centerline or axis of the acetabular cup 100. The distance X can be between a few millimeters and a few centimeters, such as between about 2 mm and about 2-3 cm. The distance X can in one implementation be no more than 3 cm, such as no more than about 2.5 cm. Therefore, the proximal surface 230D of the liner 200D is planar except for the opening above the bearing surface 210D. The location of the bearing surface 210D relative to the central axis of the acetabular cup 100 (e.g., phase change of the bearing surface 210D) can be adjusted by the surgeon before or after seating the liner 200D in the acetabular cup 100.

The impactor 300D has an impactor surface 310D corresponding to the planar proximal surface 230D of the liner 200D and has a curved (e.g., convex, spherical) impactor surface 320D corresponding to (e.g., having the same radius of curvature as) the bearing surface 210D of the liner 200D. This advantageously allows the impactor 300D to apply an impaction force square on the liner 200D relative to the acetabular cup 100 (e.g., so the center of the impaction force that is applied by the impactor 300D is located at the location of the visual indicator 240D).

Figure 8A:
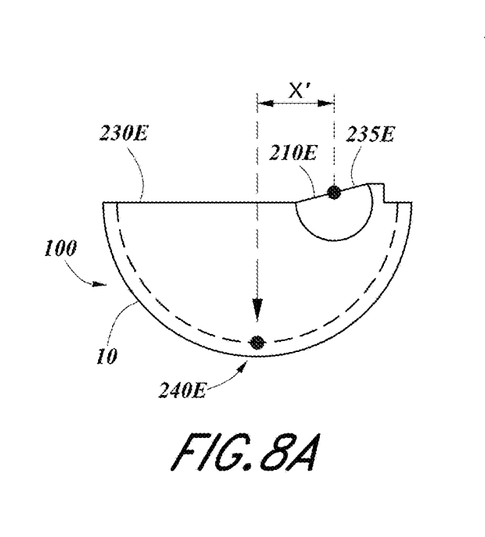
FIG. 8A is a schematic cross-sectional side view of the acetabular cup in FIG. 1 with a liner inserted in the acetabular cup, the liner having an angled face and an offset opening relative to the acetabular cup.
Figure 8B:
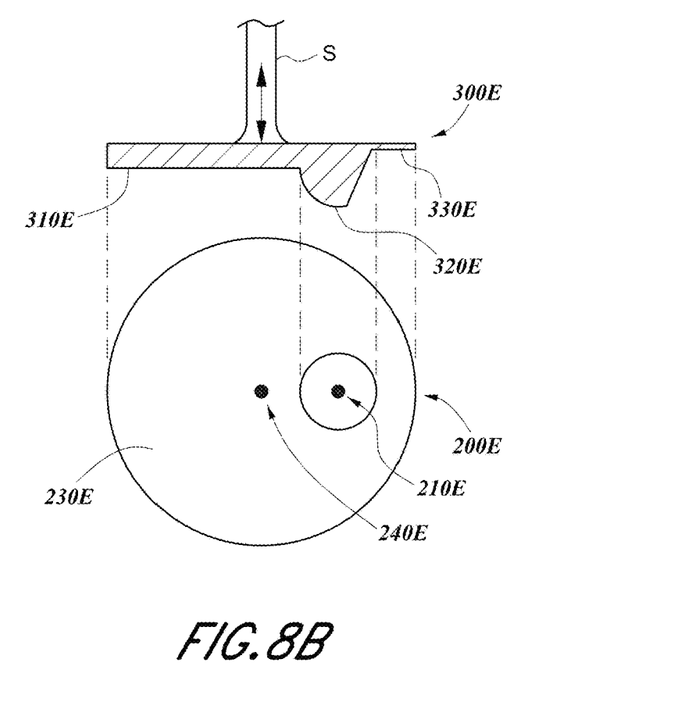
FIG. 8B is a schematic top view of the liner in FIG. 8A and a partial schematic side view of an impactor head surface to impact the liner.

FIG. 8A shows a cross-sectional side view of the liner 200E coupled to the acetabular cup 100 and FIG. 8B shows a top view of the liner 200E and an impactor 300E, which can be used to impact the liner 200E into place in the acetabular cup 100. Some of the features of the liner 200E are similar to features of the liner 200D in FIGS. 6-7B. Thus, reference numerals used to designate the various components of the liner 200E are identical to those used for identifying the corresponding components of the liner 200D in FIGS. 6-7B, except that an "E" instead of a "D" has been added to the numerical identifier. Therefore, the structure and description for the various features of the liner 200D in FIGS. 6-2B, which are based on the structure and description of the features of the liner 200 in FIGS. 2A-2B, are understood to also apply to the corresponding features of the liner 200E in FIGS. 8A-8B, except as described below. FIGS. 8A-7B are not to scale and are exaggerated to show that the center of the bearing surface of the liner 200E, and therefore the head of the femoral stem implant received therein, would be offset or off-center relative to the center of the acetabular cup 100 in two planes.

The liner 200E differs from the liner 200D in that the proximal surface 230E has an inclined portion 235E across the bearing surface 210E relative to the remainder of the proximal surface 230E. The bearing surface 210E (e.g., concave) of the liner 200E is offset from a centerline of the acetabular cup 100 so that the bearing surface 210E is not coaxial with the bearing surface 30 of the acetabular cup 100, and so that a center of the head of the femoral stem implant that is received by the bearing surface 210E would be offset or off-center (in two planes) relative to the axis or center of the acetabular cup 100. As shown in FIG. 8A, the axis of the bearing surface 210E can be offset by a distance X' from a centerline or axis of the acetabular cup 100. The distance X' can be between a few millimeters and a few centimeters, such as between about 2 mm and about 2-3 cm. The distance X' can in one implementation be no more than 3 cm, such as no more than about 2.5 cm. Therefore, the proximal surface 230E of the liner 200E has a first planar portion, an inclined portion 235E that extends at an angle from the planar portion, and an opening defined in the inclined portion 235E above the bearing surface 210E. The location of the bearing surface 210E relative to the central axis of the acetabular cup 100 (e.g., phase change of the bearing surface 210E) can be adjusted by the surgeon before or after seating the liner 200D in the acetabular cup 100. The inclined portion 235E allows the head of the femoral stem (not shown) to be further laterally offset from the acetabulum.

The impactor 300E has an impactor surface 310E corresponding to the planar proximal surface 230E of the liner 200E, a curved (e.g., convex, spherical) impactor surface 320E corresponding to (e.g., having the same radius of curvature as) the bearing surface 210E of the liner 200E, and an inclined surface 330E corresponding to the inclined portion 235E of the liner 200E. This advantageously allows the impactor 300E to apply an impaction force square on the liner 200E relative to the acetabular cup 100 (e.g., so the center of the impaction force that is applied by the impactor 300E is located at the location of the visual indicator 240E).

Figure 9:
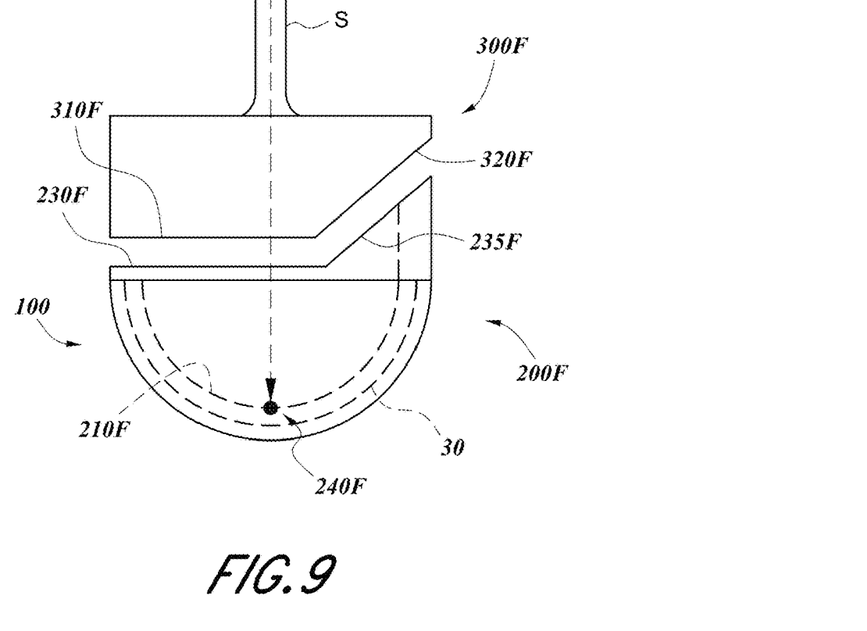
FIG. 9 is a partial schematic side view of a impactor head shape for use with a liner having a partial angled face.

FIG. 9 shows a side view of a liner 200F attached to the acetabular cup 100 and an impactor 300F, which can be used to impact the liner 200F into place in the acetabular cup 100. Some of the features of the liner 200F are similar to features of the liner 200 in FIGS. 2A-2B. Thus, reference numerals used to designate the various components of the liner 200F are identical to those used for identifying the corresponding components of the liner 200 in FIGS. 2A-2B, except that an "F" has been added to the numerical identifier. Therefore, the structure and description for the various features of the liner 200 in FIGS. 2A-2B are understood to also apply to the corresponding features of the liner 200F in FIG. 9, except as described below.

The liner 200F differs from the liner 200 in that the proximal surface 230F (e.g., outer rim) has an inclined portion 235F relative to the remainder of the proximal surface 230F. The proximal surface 230F of the liner 200F has a planar portion (e.g., portion of the outer rim defined by a plane perpendicular to an axis of the liner 200F) and an inclined portion 235F that extends at an angle from the planar portion.

The impactor 300F has an impactor surface 310F corresponding to the planar portion of the proximal surface 230F of the liner 200E and an inclined surface 320F corresponding to the inclined portion 235F of the liner 200F. This advantageously allows the impactor 300F to apply an impaction force square on the liner 200F relative to the acetabular cup 100 (e.g., so the center of the impaction force that is applied by the impactor 300F is located at the location of the visual indicator 240F).

Figure 10:
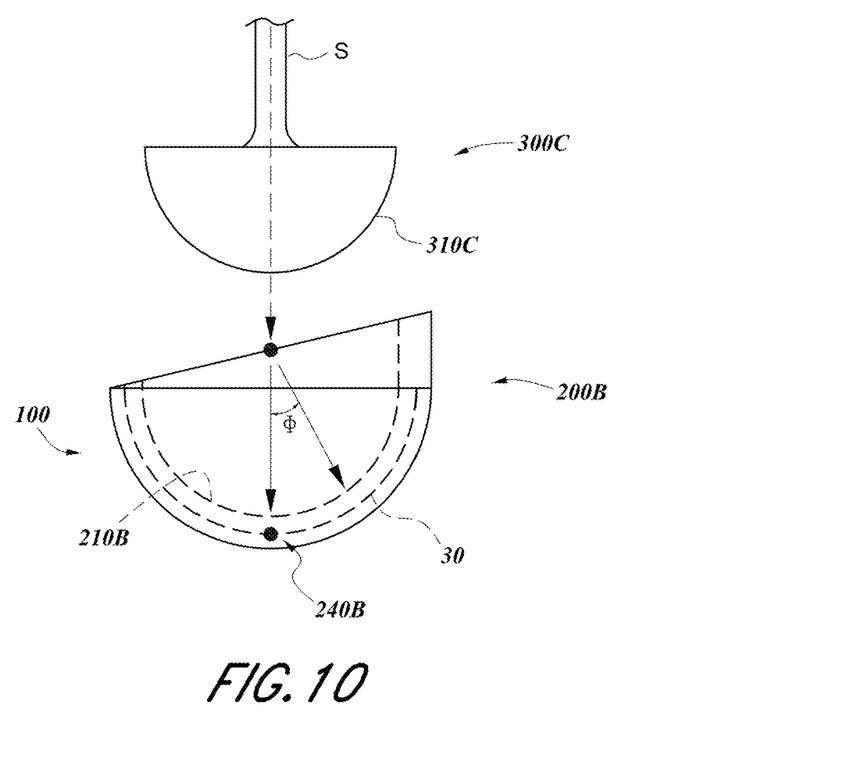
FIG. 10 is a partial schematic side view of an impactor head shape for use with a liner having an angled face.

FIG. 10 shows a side view of the liner 200B of FIGS. 4A-4B attached to the acetabular cup 100. Instead of using the impactor 300B to impact the liner 200B to seat the liner 200B in the acetabular cup 100, the impactor 300C can be used. The impactor 300C can be operated by a surgeon to apply an impaction force with the impaction surface 310C on the liner 200B on the visual indicator 240B. This advantageously allows the impactor 300C to apply an impaction force square on the liner 200B relative to the acetabular cup 100 (e.g., so the center of the impaction force that is applied by the impactor 300C is located at the location of the visual indicator 240B).

Figure 11:
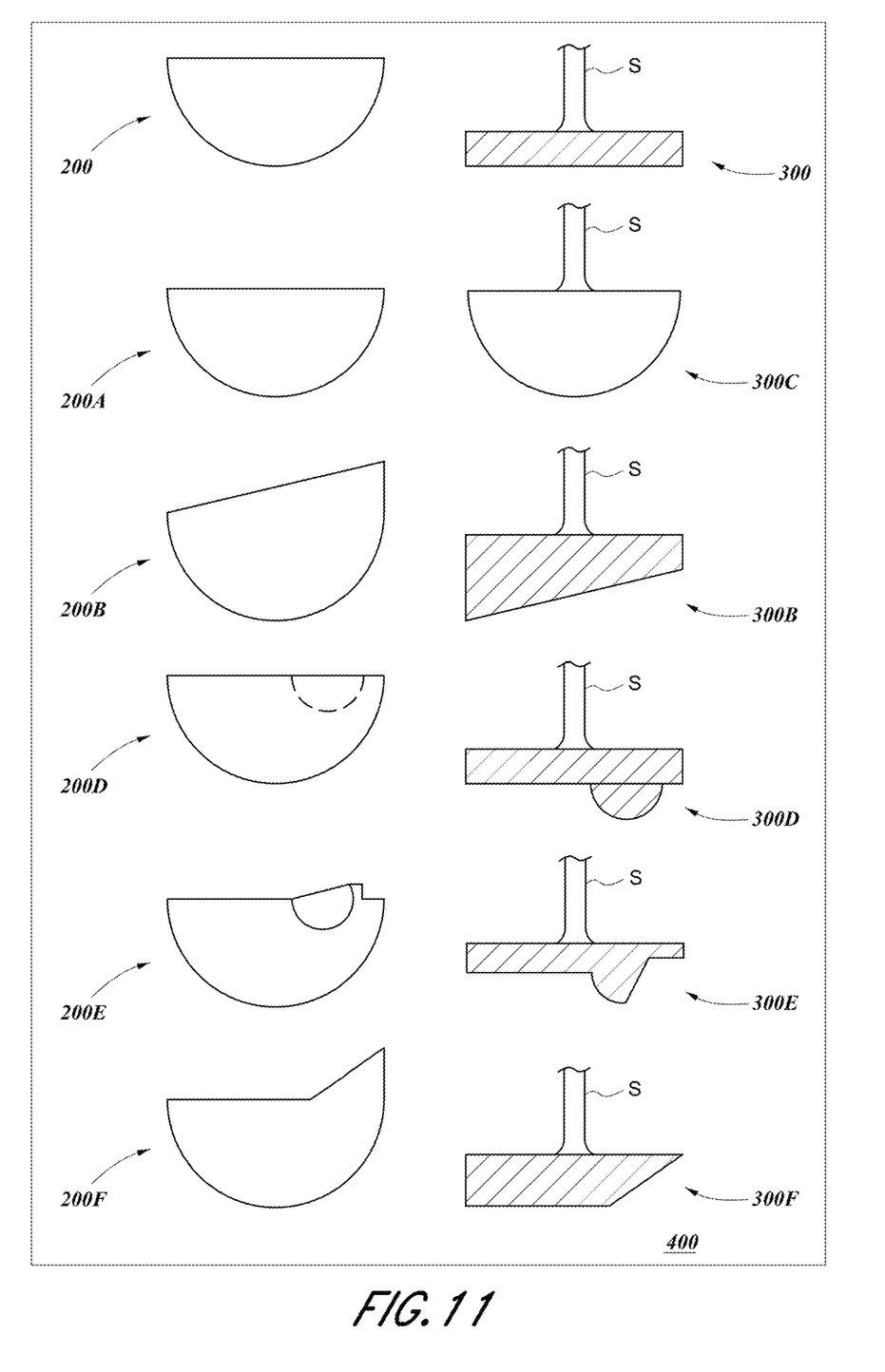
FIG. 11 is a schematic view of a liner kit for use with an acetabular cup.

FIG. 11 shows a liner kit 400 for use with an acetabular cup 100 in hip joint replacement or revision surgery. The kit 400 can include one or more of each of the liners 200, 200A, 200B, 200D, 200E, 200F disclosed herein. In one implementation, the kit 400 can also include one or more of the impactors 300, 300B, 300C, 300D, 300E, 300F disclosed herein. In one implementation, the kit 400 can also include one or more of the acetabular cups 100 sized to receive the liner 200, 200A, 200B, 200D, 200E, 200F. Advantageously, the bearing surface 30 of the acetabular cup 100 and outer surface of the liners 200, 200A, 200B, 200D, 200E, 200F allow for each of the liners 200, 200A, 200B, 200D, 200E, 200F to seat in the acetabular cup 100. In one implementation, the kit 400 has liners 200, 200A, 200B, 200D, 200E, 200F sized to correspond to a particular size acetabular cup 100. Therefore, each acetabular cup 100 of a different size can have a separate kit 400 of associated liners 200, 200A, 200B, 200D, 200E, 200F that can be used with that size acetabular cup 100. The kit 400 provides the surgeon with different liner options for use with a particular size acetabular cup 100, depending on the anatomy of the patient to provide the desired relationship between the femur and acetabulum with the hip joint replacement prosthesis.

Figure 12:
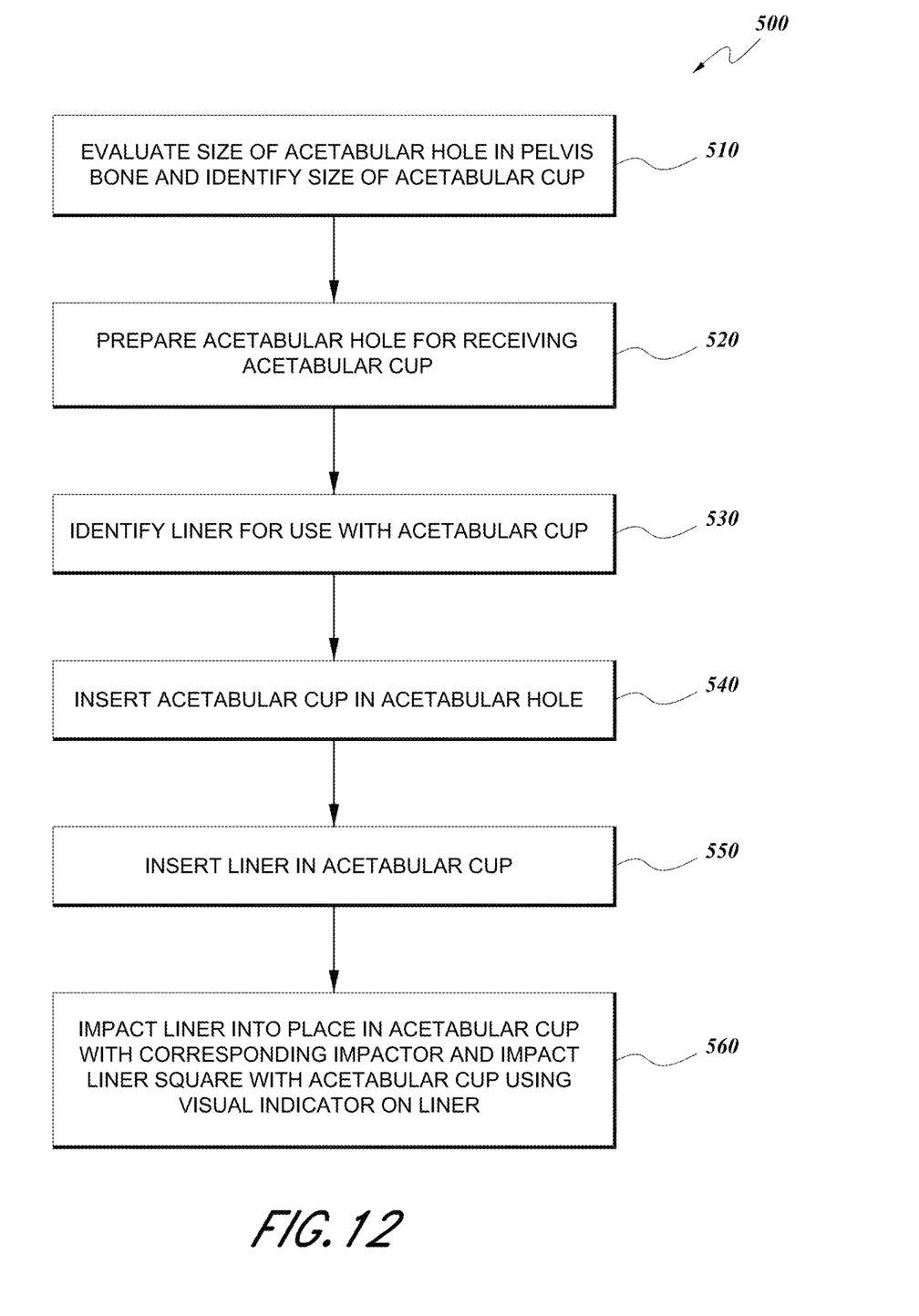
FIG. 12 is a flow chart of a method for seating a liner in an acetabular cup.

FIG. 12 shows a flow chart of a process or method 500 for using a liner, such as the liners 200, 200A, 200B, 200D, 200E, 200F disclosed herein, in hip joint replacement or revision surgery. The method 500 includes the step 510 of evaluating the size of the acetabular hole in the pelvis bone and identifying the size of acetabular cup needed for the acetabular hole. The method 500 also includes the step 520 of preparing the acetabular hole (e.g., reaming the acetabulum to create a base of vascular cancellous bone to facilitate bone growth) for receiving the acetabular cup, such as the acetabular cup 100. The method 500 also includes the step 530 of identifying the liner (such as one of the liners 200, 200A, 200B, 200D, 200E, 200F) for use with the acetabular cup (such as the acetabular cup 100). The method 500 also includes the step 540 of inserting and attaching the acetabular cup in the acetabular hole, and the step 550 of inserting the liner (such as the liner 200, 200A, 200B, 200D, 200E, 200F) in the acetabular cup. The method 500 also includes the step 560 of impacting the liner (such as the liner 200, 200A, 200B, 200D, 200E, 200F) into place (e.g., seating) within the acetabular cup with an impactor (such as the impactor 300, 300B, 300C, 300D, 300E, 300F), such that the impactor applies an impaction force on the liner square with the acetabular cup.

ADDITIONAL EMBODIMENTS

In embodiments of the present disclosure, a liner for an acetabular cup, liner and impactor system and method for implanting a liner may be in accordance with any of the following clauses:

Clause 1. A liner for an acetabular cup, comprising:
a proximal surface;
an outer convex surface configured to at least partially extend into an acetabular cup when the liner is seated in the acetabular cup;
a concave bearing surface recessed relative to the proximal surface and configured to receive a head of a femoral stem; and
one or more visual indicators on the liner configured to identify a location for applying an impaction force on the liner so that the liner is impacted square relative to the acetabular cup.

Clause 2. The liner of clause 1, wherein the one or more visual indicators are markings on the proximal surface or concave bearing surface.

Clause 3. The liner of clause 2, wherein the markings include one of cross hairs, dots and dashed lines.

Clause 4. The liner of any preceding clause, wherein the visual indicators are virtual indicators applied or projected onto the proximal surface or concave bearing surface.

Clause 5. The liner of any preceding clause, wherein the concave bearing surface extends about an axis that is offset from an axis of the acetabular cup when the liner is seated in the acetabular cup.

Clause 6. The liner of any preceding clause, wherein at least a portion of the proximal surface extends along a plane perpendicular to an axis of the acetabular cup when the liner is seated in the acetabular cup.

Clause 7. The liner of any preceding clause, wherein at least a second portion of the proximal surface extends along a second plane at an angle relative to the plane, the second portion defining an opening above the concave bearing surface.

Clause 8. The liner of any preceding clause, wherein at least a portion of the proximal surface extends along a plane perpendicular to an axis of the acetabular cup when the liner is seated in the acetabular cup.

Clause 9. The liner of any preceding clause, wherein at least a second portion of the proximal surface extends along a second plane at an angle relative to the plane, the second portion defining an opening above the concave bearing surface.

Clause 10. A liner and impactor system for an acetabular cup, comprising:
a liner comprising
a proximal surface;
an outer convex surface configured to at least partially extend into an acetabular cup when the liner is seated in the acetabular cup;
a concave bearing surface recessed relative to the proximal surface and configured to receive a head of a femoral stem; and
one or more visual indicators on the liner configured to identify a location for applying an impaction force on the liner; and an impactor having an impaction surface corresponding to one or both of the proximal surface and the concave bearing surface of the liner, the impactor configured to apply an impaction force on the liner so that the liner is impacted square relative to the acetabular cup.

Clause 11. The system of clause 10, wherein the one or more visual indicators include markings on the proximal surface or concave bearing surface.

Clause 12. The system of clause 11, wherein the markings include one of cross hairs, dots and dashed lines.

Clause 13. The system of any of clauses 10-12, wherein the visual indicators are virtual indicators applied or projected onto the proximal surface or concave bearing surface.

Clause 14. The system any of clauses 10-13, wherein the concave bearing surface extends about an axis that is offset from an axis of the acetabular cup when the liner is seated in the acetabular cup.

Clause 15. The system of any of clauses 10-14, wherein at least a portion of the proximal surface extends along a plane perpendicular to an axis of the acetabular cup when the liner is seated in the acetabular cup.

Clause 16. The system of any of clauses 10-15, wherein at least a second portion of the proximal surface extends along a second plane at an angle relative to the plane, the second portion defining an opening above the concave bearing surface.

Clause 17. The system of any of clauses 10-16, wherein at least a portion of the proximal surface extends along a plane perpendicular to an axis of the acetabular cup when the liner is seated in the acetabular cup.

Clause 18. The system of any of clauses 10-17, wherein at least a second portion of the proximal surface extends along a second plane at an angle relative to the plane, the second portion defining an opening above the concave bearing surface.

Clause 19. A method for implanting a liner in an acetabular cup, comprising:
  evaluating a size of an acetabular hole;
  identifying a size of an acetabular cup for the acetabular hole;
  preparing the acetabular hole to receive the acetabular cup;
  identifying a liner for use with the acetabular cup;
  inserting the acetabular cup in the acetabular hole;
  inserting the liner in the acetabular cup; and
  impacting the liner into place in the acetabular cup with an impactor square with the acetabular cup to seat the liner in the acetabular cup.

Clause 20. The method of clause 19, wherein impacting the liner with the impactor includes applying an impaction force on the liner so that the applied force is centered on a visual indicator on the liner.

While certain embodiments of the inventions have been described, these embodiments have been presented by way of example only, and are not intended to limit the scope of the disclosure. Indeed, the novel methods and systems described herein may be embodied in a variety of other forms. Furthermore, various omissions, substitutions and changes in the systems and methods described herein may be made without departing from the spirit of the disclosure. The accompanying claims and their equivalents are intended to cover such forms or modifications as would fall within the scope and spirit of the disclosure. Accordingly, the scope of the present inventions is defined only by reference to the appended claims.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

Of course, the foregoing description is that of certain features, aspects and advantages of the present invention, to which various changes and modifications can be made without departing from the spirit and scope of the present invention. Moreover, the devices described herein need not feature all of the objects, advantages, features and aspects discussed above. Thus, for example, those of skill in the art will recognize that the invention can be embodied or carried out in a manner that achieves or optimizes one advantage or a group of advantages as taught herein without necessarily achieving other objects or advantages as may be taught or suggested herein. In addition, while a number of variations of the invention have been shown and described in detail, other modifications and methods of use, which are within the scope of this invention, will be readily apparent to those of skill in the art based upon this disclosure. It is contemplated that various combinations or subcombinations of these specific features and aspects of embodiments may be made and still fall within the scope of the invention. Accordingly, it should be understood that various features and aspects of the disclosed embodiments can be combined with or substituted for one another in order to form varying modes of the discussed devices.

What is claimed is:

1. A liner for an acetabular cup, comprising:
    a proximal surface;
    an outer convex surface configured to at least partially extend into an acetabular cup when the liner is seated in the acetabular cup;
    a concave bearing surface recessed relative to the proximal surface and configured to receive a head of a femoral stem; and
    one or more visual indicators on the liner configured to identify a location for applying an impaction force on the liner so that the liner is impacted square relative to the acetabular cup, wherein the one or more visual indicators include markings on the concave bearing surface.

2. The liner of claim 1, wherein the one or more visual indicators include markings on the proximal surface.

3. The liner of claim 2, wherein the markings include one of cross hairs, dots and dashed lines.

4. The liner of claim 1, wherein the visual indicators are virtual indicators applied or projected onto concave bearing surface.

5. The liner of claim 1, wherein the concave bearing surface extends about an axis that is offset from an axis of the acetabular cup when the liner is seated in the acetabular cup.

6. The liner of claim 5, wherein at least a portion of the proximal surface extends along a plane perpendicular to an axis of the acetabular cup when the liner is seated in the acetabular cup.

7. The liner of claim 5, wherein at least a second portion of the proximal surface extends along a second plane at an angle relative to the plane, the second portion defining an opening above the concave bearing surface.

8. The liner of claim 1, wherein at least a portion of the proximal surface extends along a plane perpendicular to an axis of the acetabular cup when the liner is seated in the acetabular cup.

9. The liner of claim 8, wherein at least a second portion of the proximal surface extends along a second plane at an angle relative to the plane, the second portion defining an opening above the concave bearing surface.

10. A liner and impactor system for an acetabular cup, comprising:
    a liner comprising
        a proximal surface;
        an outer convex surface configured to at least partially extend into an acetabular cup when the liner is seated in the acetabular cup;
        a concave bearing surface recessed relative to the proximal surface and configured to receive a head of a femoral stem, an axis of the concave bearing surface being laterally offset relative to an axis of an acetabular cup when the liner is coupled to the acetabular cup; and
        one or more visual indicators on the liner configured to identify a location for applying an impaction force on the liner; and
    an impactor having an impaction surface corresponding to one or both of the proximal surface and the concave bearing surface of the liner, the impactor configured to apply an impaction force on the liner so that the liner is impacted square relative to the acetabular cup.

11. The system of claim 10, wherein the one or more visual indicators include markings on the proximal surface or concave bearing surface.

12. The system of claim 11, wherein the markings include one of cross hairs, dots and dashed lines.

13. The system of claim 10, wherein the visual indicators are virtual indicators applied or projected onto the proximal surface or concave bearing surface.

14. The system of claim 10, wherein the concave bearing surface extends about an axis that is offset from an axis of the acetabular cup when the liner is seated in the acetabular cup.

15. The system of claim 14, wherein at least a portion of the proximal surface extends along a plane perpendicular to an axis of the acetabular cup when the liner is seated in the acetabular cup.

16. The system of claim 14, wherein at least a second portion of the proximal surface extends along a second plane at an angle relative to the plane, the second portion defining an opening above the concave bearing surface.

17. The system of claim 10, wherein at least a portion of the proximal surface extends along a plane perpendicular to an axis of the acetabular cup when the liner is seated in the acetabular cup.

18. The system of claim 17, wherein at least a second portion of the proximal surface extends along a second plane at an angle relative to the plane, the second portion defining an opening above the concave bearing surface.

19. A method for implanting a liner in an acetabular cup, comprising:
    evaluating a size of an acetabular hole;
    identifying a size of an acetabular cup for the acetabular hole;
    preparing the acetabular hole to receive the acetabular cup;
    identifying a liner for use with the acetabular cup;
    inserting the acetabular cup in the acetabular hole;
    inserting the liner in the acetabular cup; and
    impacting the liner into place in the acetabular cup with an impactor square with the acetabular cup to seat the liner in the acetabular cup, the liner having a concave bearing surface, an axis of the concave bearing surface being laterally offset relative to an axis of an acetabular cup when the liner is coupled to the acetabular cup.

20. The method of claim 19, wherein impacting the liner with the impactor includes applying an impaction force on the liner so that the applied force is centered on a visual indicator on the liner.

\* \* \* \* \*